Figure 1:
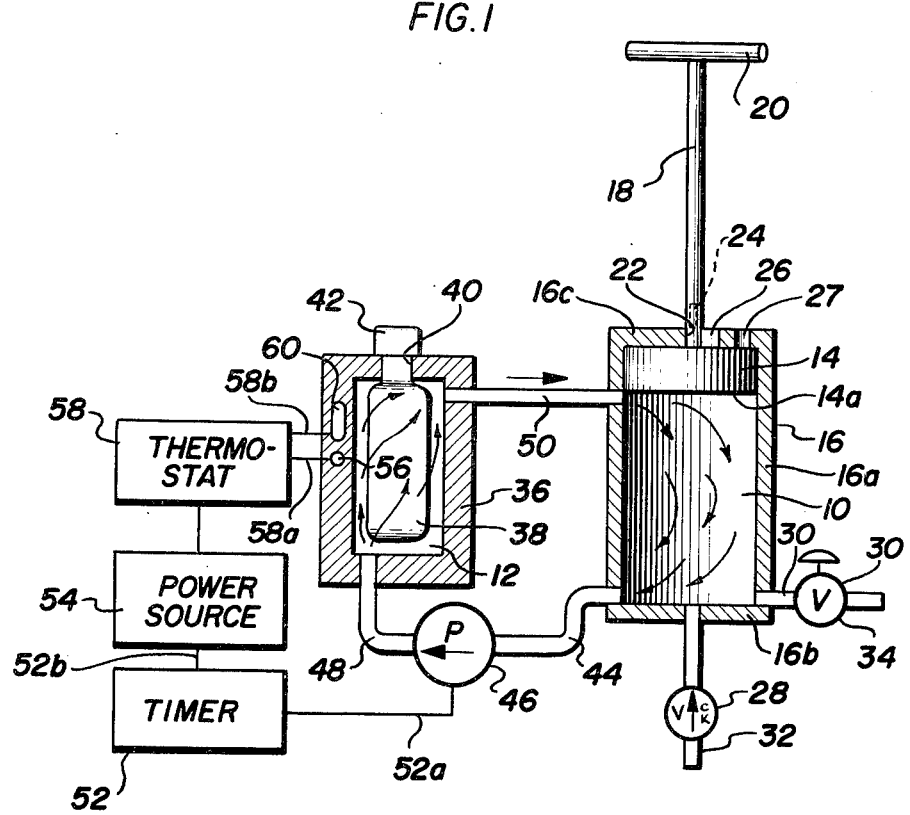

United States Patent
Hoppesch

[11] 3,948,604
[45] Apr. 6, 1976

[54] ALCOHOLIC BREATH SIMULATION SYSTEM

[75] Inventor: Joseph P. Hoppesch, Schaumburg, Ill.

[73] Assignee: Borg-Warner Corporation, Chicago, Ill.

[22] Filed: Jan. 2, 1974

[21] Appl. No.: 430,288

[52] U.S. Cl............ 23/254 R; 23/232 R; 73/422 TC
[51] Int. Cl.² ........................................ G01N 1/22
[58] Field of Search .......... 23/232 R, 254 R, 254 E; 55/16, 158, 338, 339; 73/23, 23.1, 422 R, 422 TC, 422 GC; 210/23 H

[56] References Cited
UNITED STATES PATENTS

| | | | |
|---|---|---|---|
| 2,824,789 | 2/1958 | Borkenstein | 23/232 R X |
| 2,867,511 | 1/1959 | Harger | 23/232 R X |
| 3,649,199 | 3/1972 | Littlejohn | 23/230 B |

OTHER PUBLICATIONS

*Anal. Chem.*, Vol. 42, pp. 871–876 (1970).

Primary Examiner—Morris O. Wolk
Assistant Examiner—Timothy W. Hagan
Attorney, Agent, or Firm—James J. Jennings

[57] ABSTRACT

A simulated alcoholic breath sample is provided by circulating a known volume of a gas such as air or non-alcoholic breath over the outer surface of a container filled with ethyl alcohol and maintained at a given temperature, the container having a wall permeable by ethyl alcohol at a known permeation rate. Circulation of the volume of gas is continued until the gas has the desired alcohol concentration.

9 Claims, 2 Drawing Figures

ALCOHOLIC BREATH SIMULATION SYSTEM

BACKGROUND OF THE INVENTION

A wide variety of breath testing devices have been developed for determining the content of ethyl alcohol in breath expelled from the lungs, or for determining whether the alcohol content exceeds a certain predetermined concentration. Such devices are useful in identifying the inebriate, since it is generally accepted that the alochol content of the breath is directly related to the blood alcohol content (B.A.C.). In order to calibrate such devices or to determine whether they are functioning properly, they may be tested by means of a simulated breath sample or standard having a known alcohol concentration. The operation of some breath testing devices requires a reference breath sample of known alcohol concentration each time the device is used, the reference sample being compared to the breath expelled by the subject.

Precise control of the alcohol concentration in a breath sample has been difficult to achieve. Many previously known methods and systems for preparing or producing alcoholic breath samples require a number of intricate steps to be performed and may also call for elaborate laboratory equipment. Operation in accordance with the present invention, on the other hand, is extremely simple, and the disclosed alcohol and breath simulation system may be made relatively compact and portable. It may also be readily incorporated within the breath testing device with which it is to be used.

SUMMARY OF THE INVENTION

In accordance with the present invention, a sample of simulated alcoholic breath, having a predetermined concentration of ethyl alcohol, is prepared by introducing ethyl alcohol into a container having at least a portion of a wall thereof permeable to the alcohol. The alcohol in the container is maintained at a given temperature, and a known volume of gas is circulated over the wall portion for a period of time determined by the permeation rate of the container wall. Means are provided for carrying out such procedure.

Precise control of the alcohol concentration is made possible by using a permeable material which has a constant permeation rate under uniform conditions. A concise exposition of the useful properties of such materials is given in A. E. O'Keeffe and G. C. Ortman, "Primary Standards for Trace Gas Analysis," *Analytical Chemistry*, Vol. 38, No. 6 (May 1966), p. 760.

THE DRAWINGS

Figure 2:
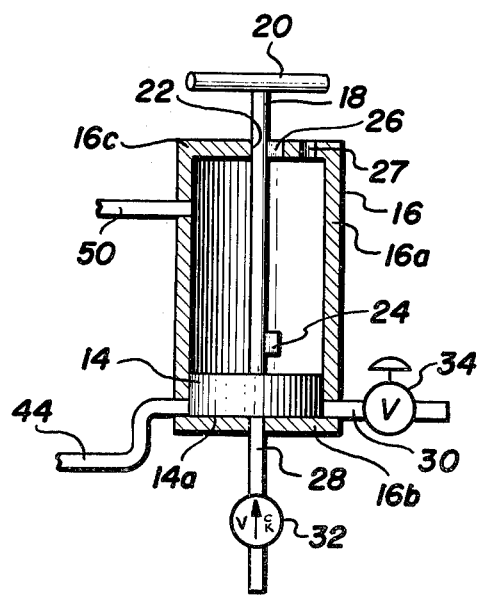

In the drawings:

FIG. 1 is a schematic representation of an alcoholic breath simulation system constructed and adapted to operate in accordance with the invention, and shows an element of the system in a first position; and FIG. 2 is a partial representation of the system of FIG. 1, showing the same element in a second position.

THE PREFERRED EMBODIMENT

Referring to the drawings, a gas reservoir 10 and an alcohol chamber 12 are connected in a closed circuit. Gas reservoir 10 is formed when a piston 14 is moved to the position shown in FIG. 1 and is defined by the underside 14a of the piston, a lateral wall 16a of a cylinder 16 in which the piston is received, and a lower wall 16b of the cylinder. Cylinder 16 is shown in FIGS. 1 and 2 in a section taken through its axis.

Piston 14 may be moved between the positions shown in FIGS. 1 and 2, respectively, by means of a piston rod 18 fixed to the piston, and a handle 20 carried by the piston rod. Piston rod 18 extends through an opening 22 provided in an upper wall 16c of cylinder 16. Piston 14 may be secured in the position shown in FIG. 1 by any suitable means, represented in the drawings as a latch 24 which is drawn through a slot 26 communicating with opening 22 and then rotated a quarter-turn to the position shown in interrupted lines in FIG. 1 to engage the outer surface of upper cylinder wall 16c.

Cylinder 16 is provided with a gas inlet 28 and a gas outlet 30. Flow through gas inlet 28 is controlled by a check valve 32 which permits flow in only one direction, as represented by an arrow. Gas flow through outlet 30 is controlled by a manually actuated valve 34 movable between a closed position permitting flow through outlet 30, a fully open position permitting unrestricted flow of gas through outlet 30, and an infinite number of positions therebetween. If desired, valve 34 may be replaced by a check valve permitting flow through outlet 30 only in the outward direction relative to gas reservoir 10. Upper wall 16c of the cylinder is provided with a vent 27 to facilitate movement of piston 14.

Alcohol chamber 12 is defined by a wall 36 of any suitable configuration such as that shown in FIG. 1 in a section taken through its longitudinal axis. Suspended or supported within alcohol chamber 12 is an alcohol container comprising a vial or flask 38 which will be described with greater particularity hereinafter. An opening 40 is provided in wall 36 to provide access to the interior of flask 38, and the flask is provided with a removable closure 42 accessible from the exterior of wall 36. Any suitable means (not shown) may be provided for removing flask 38 from chamber 12 and replacing it therein. Sealing means (also not shown) may be provided at opening 40 to maintain alcohol chamber 12 gastight. Flask 38 is so supported in alcohol chamber 12 that at least a portion of the flask wall is spaced from the chamber wall 36.

A gas conduit 44 provides a passage between gas reservoir 10 and the inlet of a pump 46. A second gas conduit 48 interconnects alcohol chamber 12 and the outlet of pump 46. A third gas conduit 50 interconnects alcohol chamber 12 and gas reservoir 10 directly. However, if desired, isolation valves (not shown) may be provided in conduits 44 and 50 to control flow therethrough.

Operation of pump 46 is controlled by a timer 52 connected thereto by any suitable means 52a. Timer 52, in turn, is connected by any suitable means 52b to a source 54 of electrical power.

Chamber wall 36 is provided with an electrical heating means, represented schematically at 56, which acts to heat chamber 12 and thus flask 38 and its contents. Heating means 56 is controlled by a thermostat 58 which is connected thereto by any suitable means 58a and which acts to maintain the flask and its contents at a constant temperature. Thermostat 58 is also connnected by any suitable means 58b to a temperature sensor 60. While sensor 60 is shown embedded in chamber wall 36, for more precise temperature control it may be placed within alcohol chamber 12, or for still more precise control, within flask 38. Thermostat 58 is connected by any suitable means 58c to power source 54.

Pump 46 is preferably of the constant-flow type, such as the Gas Sampling Pump, Model AS-100, manufactured by Spectrex Co. of Redwood City, California. The latter pump is especially suitable because, while it has a capacity of 1 liter per minute, it can be contained in a cubic space measuring two inches on a side, and it incorporates an electronic drive system in place of the more conventional motor and gear assembly.

For clarity of illustration, the major elements of the system are shown spaced from one another in FIG. 1. However, they are preferably arranged in compact fashion within a single housing, suitable electrical and thermal insulation being provided where necessary or desirable. Similarly, the longitudinal dimensions of conduits 44, 48 and 50 are exaggerated in FIG. 1 and can be reduced to the extent that the conduits amount to little more than ports providing communication between gas reservoir 10, pump 46 and alcohol chamber 12.

If the system of FIG. 1 is to be used to calibrate a single breath testing device, or to provide a reference gas therefor, it may be incorporated within the housing of the breath testing device, outlet 30 being permanently connected to an appropriate inlet of the device.

Gas inlet 28 and the associated check valve 32 may be omitted, especially if the breath simulation system comprises a separate unit, in which case gas outlet 30 may also serve as an inlet.

Turning now to flask 38, the wall thereof, or at least a portion of the wall, is formed of a material permeable by ethyl alcohol. Materials suitable for this prupose include FEP Teflon (fluorinated ethylene-propylene polymer) and silicone elastomers. The permeation rate is dependent on temperature and the area of the permeable surface, but is virtually independent of the thickness of the permeable material. The permeation rate can be calculated by determining the weight of alcohol lost from flask 38 over a measured period of time under expected conditions of temperature and humidity. This, as well as other methods of calibration, are described with particularity in the aforementioned article by O'Keeffe and Ortman.

OPERATION

Operation of the alcoholic breath simulation system is quite simple and is described as follows.

Closure 42, which is preferably not permeable to ethyl alcohol, is removed and flask 38 is filled with ethyl alcohol or the commercially available 95 percent concentration thereof in distilled water (190 proof). Closure 42 is then replaced and heating means 56, which may be a simple electrical heating element encircling alcohol chamber 12, is energized from power source 54 by way of thermostat 58 to raise the temperature of the alcohol to the desired level. Thermostat 58 is preferably adjustable to select a desired temperature, say 34°C. (which is the approximate temperature of human breath). When the desired temperature level has been achieved, piston 14 is raised from the position shown in FIG. 2 to the position shown in FIG. 1 to draw a carrier gas into cylinder 16 by way of gas inlet 32 and check valve 28. The carrier gas may be ambient air, or it may be breath known to be non-alcoholic and previously expelled into a bag (not shown) placed in communication with inlet 32. The raising of the piston will also establish gas reservoir 10, the dimensions of which can be determined to calculate the precise volume of gas contained therein. Handle 20, and thus latch 24, is rotated to secure piston 14 in the position shown in FIG. 1.

Valve 34 being closed throughout the foregoing procedure, pump 46 is energized from power source 54 by way of timer 52. Timer 52 is adjustable to select the period of operation of the pump and thereby select the concentration of alcohol in the breath sample to be provided, as explained hereinbelow.

When pump 46 is energized, carrier gas will be circulated in the closed circuit. More particularly, it will be drawn from gas reservoir 10 into alcohol chamber 12 by way of the pump and conduits 44 and 48, and from alcohol chamber 12 to gas reservoir 10 by way of conduit 50. In traversing alcohol chamber 12, the gas will be drawn over the outer surface of the alcohol-permeable wall defining flask 38, as indicated by arrows in FIG. 1, to be enriched by alcoholic vapor. The enriched gas will be mixed with the gas in gas reservoir 10, also as indicated by arrows, ultimately to provide the desired breath sample.

When the selected period of operation of pump 46 has elapsed, timer 52 will act to de-energize the pump and thus halt circulation between gas reservoir 10 and alcohol chamber 12.

Handle 20 is now rotated to align latch 24 with slot 26, valve 34 is opened, and piston 14 is lowered to the position shown in FIG. 2 to evacuate the alcoholic breath sample from cylinder 16, the sample being directed from outlet 30 to an appropriate inlet of a breath testing device.

Before operating the system it may be advisable to energize the pump briefly and raise and lower piston 14 several times to remove residual gas.

It will be obvious that the concentration of alcohol in the breath sample will be dependent on the period of operation of pump 46. Thus, by way of example, assuming that the wall of flask 38 has a permeation rate of 60 micrograms per minute, that gas reservoir 10 has a volume of 500 milliliters, a breath sample having an alcohol concentration equivalent to 0.10% B.A.C. (blood alcohol content) will require operation of the pump for approximately 4 minutes. Approximately eight minutes of operation will yield a sample equivalent to 0.20% B.A.C. The precise periods of operation may be determined by calibration or direct calibration, as by using any of a number of well known methods of ascertaining the alcohol concentration in a gas.

While the invention has been described in connection with a specific embodiment thereof, it is to be understood that this is by way of illustration and not by way of limitation; and the scope of the appended claims should be construed as broadly as the prior art will permit.

What is claimed is:

1. An alcoholic breath simulation system comprising a wall defining an alcohol container, the wall having at least a portion thereof permeable by ethyl alcohol, the wall portion having an inner surface exposed to ethyl alcohol when ethyl alcohol is introduced into the container, the wall portion also having an outer surface, means surrounding the container to define an alcohol chamber with the container supported in the chamber and with the wall portion spaced from the chamber-defining means, means defining a gas reservoir adapted to enclose a predetermined volume of gas, the alcohol chamber and the gas reservoir being connected in a closed gas circuit, and pump means associated with the gas circuit and operable to circulate gas therein from the gas reservoir to the alcohol chamber, over the outer surface of the container wall portion, and from the alcohol chamber to the gas reservoir to complete the circuit.

2. The alcoholic breath simulation system according to claim 1, including timing means associated with the pump means and operable to de-energize the pump means when a predetermined period of time has elapsed.

3. The alcoholic breath simulation system according to claim 2, wherein the timing means is adjustable to vary said predetermined period of time.

4. The alcoholic breath simulation system according to claim 1, including heating means and thermostat means associated with the heating means and cooperating therewith to maintain the container and its contents at a constant predetermined temperature.

5. The alcoholic breath simulation system according to claim 1, including means for evacuating the predetermined volume of gas from the gas reservoir.

6. The alcoholic breath simulation system according to claim 5, wherein the evacuating means includes piston-cylinder means.

7. The alcoholic breath simulation system according to claim 1, wherein the container wall portion is formed of a fluorinated ethylene-propylene polymer.

8. The alcoholic breath simulation system according to claim 1, wherein the container wall portion is formed of a silicone elastomer.

9. The alcoholic breath simulation system according to claim 1, wherein the container includes a removable closure positioned externally of the alcohol chamber to provide access to the interior of the container.

* * * * *